United States Patent
Li et al.

(12)

(10) Patent No.: US 6,426,061 B1
(45) Date of Patent: Jul. 30, 2002

(54) METHOD AND COMPOSITION FOR PREVENTING SWEAT-RELATED ODOR

(76) Inventors: Weiwei Li; Min Liu, both of 345 E. 68th St. #1B, New York, NY (US) 10021

( * ) Notice: Subject to any disclaimer, the term of this patent is extended or adjusted under 35 U.S.C. 154(b) by 0 days.

(21) Appl. No.: 09/839,902

(22) Filed: Apr. 20, 2001

(51) Int. Cl.⁷ .............................. A61K 7/00; A61K 7/32; A61K 7/34; A61K 7/36; A61K 7/38
(52) U.S. Cl. .............................. 424/65; 424/66; 424/67; 424/68; 424/401
(58) Field of Search .............................. 424/65, 66, 67, 424/68, 401

(56) References Cited

U.S. PATENT DOCUMENTS 6,010,687 A * 1/2000 Cox et al. ..................... 424/65

* cited by examiner

*Primary Examiner*—Barbara P. Badio

(57) ABSTRACT

This invention involves a method for preventing sweat-related odor by using a deodorant composition to rationally interfere different steps of sweat-related odor-producing course for topical application to human skin characterized in that it contains an inhibitor of androgen receptor expression and an inhibitor of apolipoprotein D, a carrier of human odorant.

6 Claims, 3 Drawing Sheets

METHOD AND COMPOSITION FOR PREVENTING SWEAT-RELATED ODOR

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

1. Field of the Invention

The invention relates to a composition for preventing sweat-related odor by interfering with different steps of the odor-producing course, particularly by the inhibition of the androgen receptor expression and human odorant carrier proteins.

2. Description of the Related Art

Formation of body odor especially axillary odor results mainly from exceptional odor-producing abilities in the areas of body. These abilities include the following:

1) There arc increased apocrine sweat glands in these areas, which are comprised of ducts that open directly into the hair follicle and become functional at puberty. It is known that there is a high level of 5alpha-reductase activity in human apocrine glands of which type-1 5alpha-reductase is predominant. 5alpha-reductase converts testosterone (T) to dihydrotestoserone (DHT) and may play a central role in the apocrine gland development and function from the beginning of puberty. The androgen receptor levels were also found to be high in the apocrine gland of patients with osnidrosis. These observations indicate that the activity of androgens is involved with the functions of apocrine sweat glands.

2) Sweat secreted from apocrine sweat glands contains numerous substances, which are most likely the precursors for forming odoriferous compounds, even although these precursors are odorless. These precursors mainly consist of (1) volatile odor-producing steroids such as dehydroepiandrosterone (DHEA), 5α-androst-16-en-3-one (androstenone), and 5α-androst-16-en-3α-ol (adrostenol); (2) nonvolatile steroid sulfates such as dehydroepiandrosterone sulfate (DHEAS), which can be bacterially converted to odorous adrostenol; (3) volatile short-chain fatty acids, especially (E)-3-methyl-2 hegemonic acid (E-3M2H), and cholesterol esters. It is demonstrated that E-3M2H is presented in far greater quantities than volatile odoriferous steroids in apocrine secretions (700:1), although both have similar olfactory thresholds; and (4) sulfur-containing amino acids. Apocrine gland cells may take up these precursors from serum and/or enzymatically formed in apocrine gland cells.

3) Odorless apocrine precursors are transported to the skin surface by odorant carrier proteins. A main odor-producing precursor E-3M2H can be carried to the skin surface by binding to apolipoprotein D (apoD). ApoD is expressed in apocrine sweat glands as an apocrine secretion odor-binding protein (ASOB2). ASOB2 is glycoprotein and found to be glycosylated for their functions. Some of androgens such as dihydrotestosterone (DHT) can significantly increase the expression of apoD.

4) Odorless apocrine precursors carried onto the skin surface interact with the microflora in areas of body such as the underarm to cause the characteristic odor. It is demonstrated that the nature and intensity of malodor correlate with microbial populations and counts, At least two different kinds of Gram-positive bacteria metabolize odorless precursors to be odoriferous substances. Lipophilic diphtheroids cause the steroid odor by metabolizing androstenone, if the population of micrococci is staphylococcus epidermis, the odor of isovaleric acid could be apparent because of metabolizing fatty acid. Some anaerobic Gram-negative bacteria may also contribute to malodor by using sulfur-containing amino acids to generate the volatile sulfur-containing compounds (VSC). In general, mixed odor of the steroids and short-chain fatty acids may characterize the axillary region.

Deodorant products in the market are typically based on three principles to control body odor, especially in the underarm regions: (1) reduce perspiration; (2) inhibit bacterial growth; and (3) cover malodor. These products show that they have some effects on reducing unpleasant body odor. However they still have considerable disadvantages. First, effective period of these products is very limited. For example, an active component in commercial products for reducing perspiration is aluminum salt, which blocks the sweat gland ducts and only causes a 50% of perspiration reduction. Antimicrobial agents in these products reduce the number of microorganisms on the surface of the local skin. However the effect obtained with the antimicrobial agents are easily reversed by the recovery of microflora numbers. Next, the active components in the products often cause irritation, burning, itching, and other uncomfortable sensations to some people with sensitive skin. Lowering the amounts of active components in the products may reduce irritation but it may also result in impaired efficiency. Therefore, there remains a need for improved products.

An ideal composition for preventing sweat-related odor should be able to: (1) maximally attenuate functions of the apocrine sweat glands including gland development, maintenance and secretion; (2) reduce uptake and formation of odor-producing precursors; (3) reduce transport of odor-producing precursors to skin surface; (4) block apocrine gland ducts to decrease sweating moisture on the skin surface; (5) inhibit bacteria activities including suppression of enzymatic metabolites which may convert: the odorless precursors to odoriferous substances; and (6) prevent possible irritation of skin. A deodorant composition with these functions would be more potent, safer, and long-lasting.

BRIEF SUMMARY OF THE INVENTION

This invention is based on the finding that the sweat-related odor is produced mainly through an increase in the odor-producing precursors from the apocrine gland and consequent transport of odor-producing precursors to skin surface to for in malodor after interacting with the microflora. According to this invention, it has been found that a composition, when topically applied to body parts such as the underarm, prevents sweat-related odor by interfering with the odor-producing course. This invention is capable of attenuating functions of the apocrine sweat glands, reducing sweating moisture on the skin surface and bacteria activities. This invention may be more specifically regarded as inhibiting transport of odor producing precursors to the skin surface.

DETAILED DESCRIPTION OF THE INVENTION

Figure 1:
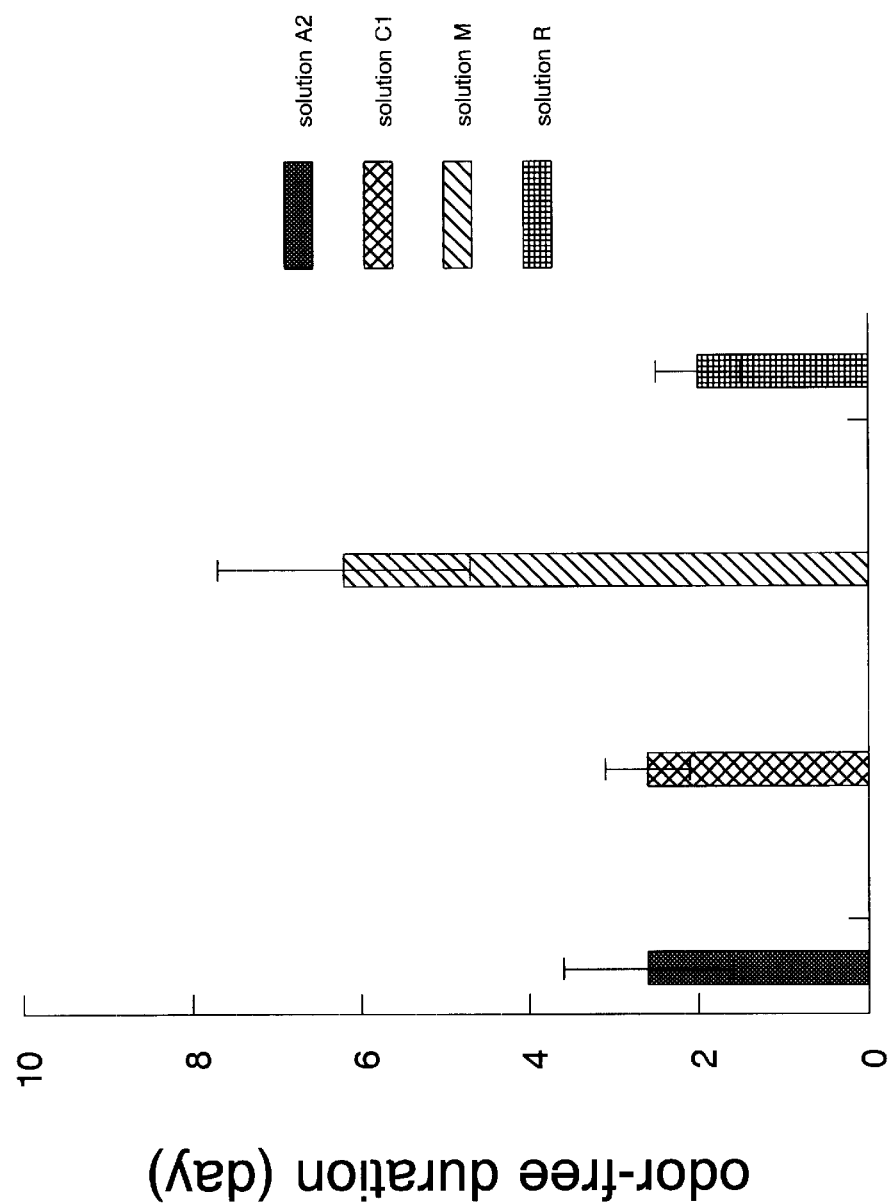
FIG. 1 is a graph of the deodorant effect of 8.2% aluminum chlorohydrate (solution A2), 0.4% chlrhexidine digluconate (solution C1), 0.4% monensin (solution M), or 0.1% resveratrol (solution R) alone. The test was carried out as described in Example 2.

The present invention is to provide an improved deodorant composition comprising an inhibitor of androgen receptor expression and an inhibitor of odorant carrier proteins to achieve the greater effect while also being safer and longer in controlling body odor through the suppression of the functions of apocrine sweat glands, reduction of odor-producing precursors, blockade of transport of odor-producing precursors to skin surface, decrease in sweating moisture on the skin surface, inhibition of bacteria activity, and the prevention of possible skin irritation.

The composition of the present invention in addition to a) an inhibitor of androgen receptor expression selected from resveratrol, epigallocatechin-3-galate and flufenamic acid in an amount from 0.01% to 10% by weight of the composition; and b) an inhibitor of odorant carrier proteins selected from monensin, tunicamycin, amphmycin, diumycin, showdomycin, tsushimycin, amphortericine, mycospocidin, streptovirudin and D-glucosamine in an amount from 0.01% to 5% by weight of the composition, contains c) a substance of anti-DHT activity selected from zinc gluconate, zinc glycerinate, zinc acetate, zinc sulfate, zinc oxide, zinc citrate and zinc chloride in amount from 0.01% to 5% by weight of the composition; d) an antiperspirant selected from aluminum chlorohydrate, aluminum chloride and aluminum zirconium in an amount from 0.0% to 40% by weight of the composition; e) an antimicrobial agent selected from chlorhexidine digluconate and chlorhexidine diacetate in an amount from 0.001% to 1% by weight of the composition and f) a cosmetically acceptable carrier.

Resveratrol, a phytoalexin, can be commercially obtained, isolated from grape skins, ground nuts, or wine, or chemically synthesized. Resveratrol was found to inhibit the expression and function of the androgen receptor in prostate cancer cells (Mitchell et al., Cancer Res, 59: 5892–5895, 1999), thereby inhibiting androgen-stimulated cell growth and gene expression. Therefore, resveratrol is able to interfere with the development and functions of apocrine sweat gland, as apocrine sweat is an androgen-targeted organ. In addition resveratrol has been shown to mediate anti-inflammatory effect by inhibiting cycloxygenase and by blocking the release or activation of inflammatory mediators such as TNF-α, NF-kB from cells stimulated with chemical irradiators. Thus anti-allergic or anti-irritating effect of resveratrol would be also expected.

Monensin is an ionophore commercially available and prevents the terminal glycosylation reaction by inhibiting N-linked oligosaccharide processing, thereby inhibiting the synthesis of glycoproteins (Machamer et al., Proc. Natl. Acad. Sci. USA, 81: 1297–1291, 1984). Monensin also inhibits the transport of membrane glycoproteins and decreases secretion of apo D from cells (Patel et al., Neuroreport, 6: 653–657, 1995). Therefore monensin can suppress the function of apo D as the odorant carrier since apo D is a glycoprotein and its function requires the glycosylation. Monensin was also found to inhibit the transport of dehydroepiandrosterone sulfate into cells.

The aluminum chlorohydrate is a well-known antiperspirant agent and is commercially available under the name of Locrono from Hoechst AG of Frankfurt FRG. The antiperspirant effect of the aluminum chlorohydrate may be done by blocking the sweat glands through aluminum-containing conglomerates in the duct within the upper epidermis.

The use of zinc salt such as zinc oxide and zinc sulfate to block DHT activity to inhibit growth of androgen-targeted cells was described as early as 1990 (U.S. Pat. No. 4,946,688). In addition, Zinc can bind and complex to polymers of carboxyl sulfate, phosphate and oxidizes thiol groups to inhibit production of odoriferous VSC generated by anaerobic gram negative-bacteria.

Chlorhexidine, a bisdiguanide, is commercially available under the trade name Hibitane as a cationic anti bacterial agent. The use of chlorhexidine in deodorant compositions is described in U.S. Pat. No. 6,010,687. Because the lipid materials significantly inhibit the anti bacterial effect of chlorhexidine, reduction of lipid materials such as fatty acid in the underarm by blocking their excretion to skin surface with monensin and aluminum chlorohydrate can enhance the effect of chlorhexidine. The combination of chlorhexidine with zinc salt was also found to be superior in anti bacterial antiplaque action when compared to chlorhexidine alone.

The use of aluminum chlorohydrate in combination with odor-masking substances and antimicrobial agents for producing deodorant compositions is known from prior art. We have surprisingly discovered that this invention by combining resveratrol, monensin, and chlorhexidine digluconate with aluminum chlorohydrate and zinc provides greater and longer-lasting effects than expected in preventing or controlling malodor. We also discovered that addition of resveratrol is useful in preventing irritation probably induced by aluminum salt. We further discovered that topical application of composition B (aluminum chlorohydrate, zinc sulfate, resveratrol and monensin) followed by chlorhexidine diacetate dramatically controlled malodor for as long as 21 days.

In this invention, the deodorant active material is dissolved in a cosmetically acceptable carrier to provide a deodorant composition to prevent sweat-related odor under armpit and/or other areas of skill. The carrier material for the composition can comprise one or more volatile carrier fluids if required. In practice, the invention composition may preferably contain low molecular weight aliphatic alcohol such as ethanol. Ethanol proportion in the composition may be selected within the range of from 10–90% by weight. Other cosmetically acceptable carrier materials can comprise a liquid or a mixture of fluids such as low molecular weight hydrocarbons, water and volatile low viscosity silicones, selected according to the physical form of the cosmetic vehicles. The cosmetic vehicles can be in the form of a fluid, cream, lotion, gel stick or spray, but preferably in the form of a fluid.

The deodorant composition of the prevent invention will now be illustrated in detail by the following examples:

EXAMPLE 1

The following is a formulation of composition A and B prepared in the form of a liquid deodorant according to the invention.

| ingredient | % by weight |
|---|---|
| Composition A | |
| Resveratrol | 0.1 |
| Monensin | 0.4 |
| Aluminum chlorohydrate | 8.2 |
| Zinc sulphate | 0.5 |
| Chlorhexidine digluconate | 0.04 |
| Ethanol | 60 |
| Water | 30.8 |
| Composition B | |
| Resveratrol | 0.1 |
| Monensin | 0.4 |
| Zinc sulphate | 0.5 |
| Aluminum chlorohydrate | 8.2 |
| Ethanol | 60 |
| Water | 30.8 |

EXAMPLE 2

A test for the deodorant effects of monensin or resveratrol alone was first carried out. The positive controls were 8.2% aluminum chlorohydrate, a level that is used in most deodorant or antiperspirant products on the market and 0.4% chlorhexidine digluconate, a level that is usually used for bacterial killing. The negative control was a vehicle consisting of 60% ethanol and 40% water. Three experienced underarm odor assessors who are able to correctly rank the odor intensities based on the deodorant value test system U.S. Pat. No. 4,278,658) performed odor assessments. I)odorant assessment scores were recorded according to the inalodor category scale, when applied directly to the axillae skin of a panel of human subjects.

| | Malodor category Scale | |
|---|---|---|
| Score | description of odor | conc. of isovaleric acid solution (ml/L) |
| 0 | no odor | 0 |
| 1 | slight | 0.013 |
| 2 | definite | 0.053 |
| 3 | moderate | 0.22 |
| 4 | strong | 0.87 |
| 5 | very strong | 3.57 |

The test described in deodorant value test system has been modified by measuring odor intensity every 24 hours after treatment until odor intensity is detectable (score 1 or up) on a 0–5 score instead of just 24 hours after treatment.

In this test, twenty subjects selected by experienced odor assessors have an average odor score of 3.5 (range from score 3–5). To prevent any any-over effects from occurring, all of subjects have not used any underarm products before test for at least 10 days. Twenty subjects were randomly divided into 4 groups (five subjects/each group) to test the composition containing monensin or resveratrol and the positive control products. Before testing, the subjects were instructed to take a shower in the evening using ordinary soap to clean the body surfaces. After the skin was dried the different solutions were topically tested in one axilla, versus control vehicle in the other. The subjects then go about their normal business. At 24 hour intervals, each subject was evaluated for underarm odor by averaging the score of the three assessors until odor in test groups was detectable (score 1 or up). A summary of the results of the test is given in FIG. 1 The solution containing monensin was more effective in preventing underarm odor than the positive control products.

EXAMPLE 3

Figure 2:
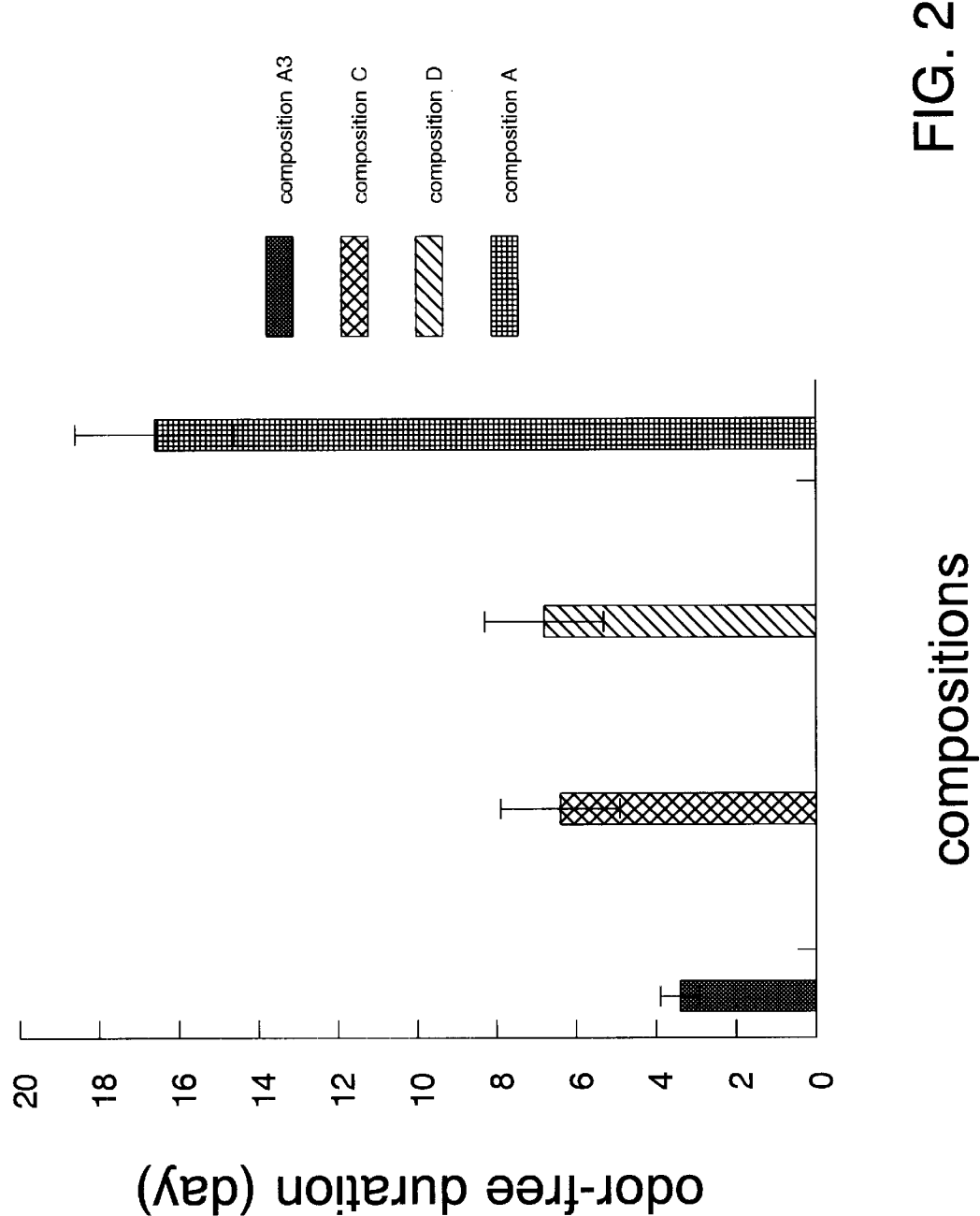
FIG. 2 is a graph of the deodorant effect of composition A (resveratrol, monensin, aluminum chlorohydrate, Zinc sulfate and chlorhexidine digluconate), composition C (8.2% aluminum chlorohydrate, 0.5% zinc sulfate and 0.04% chlorhexidine digluconate), composition D (0.4% monensin and 0.1% resveratrol), or composition A3 (8.2% aluminum chlorohydrate and 0.5% zinc sulfate). The test was carried out as described in Example 3.

Under the same test conditions described in Example 2, twenty subjects were divided into 4 groups (five subjects/each group) to test composition A, C (aluminum chlorohydrate, zinc sulfate and chlorhexidine digluconate ), D (monensin plus resveratrol) and the positive control product A3 (8.2% Aluminum chlorohydrate plus 0.5% zinc sulfate). A summary of the results of the test is given in FIG. 2. Composition A was markedly more effective in preventing underarm odor than the positive control and other compositions. Composition A of the present invention was also associated with no skin irritation in tested subjects, while the control product caused temporary underarm itching in two of the five subjects.

EXAMPLE 4

Figure 3:
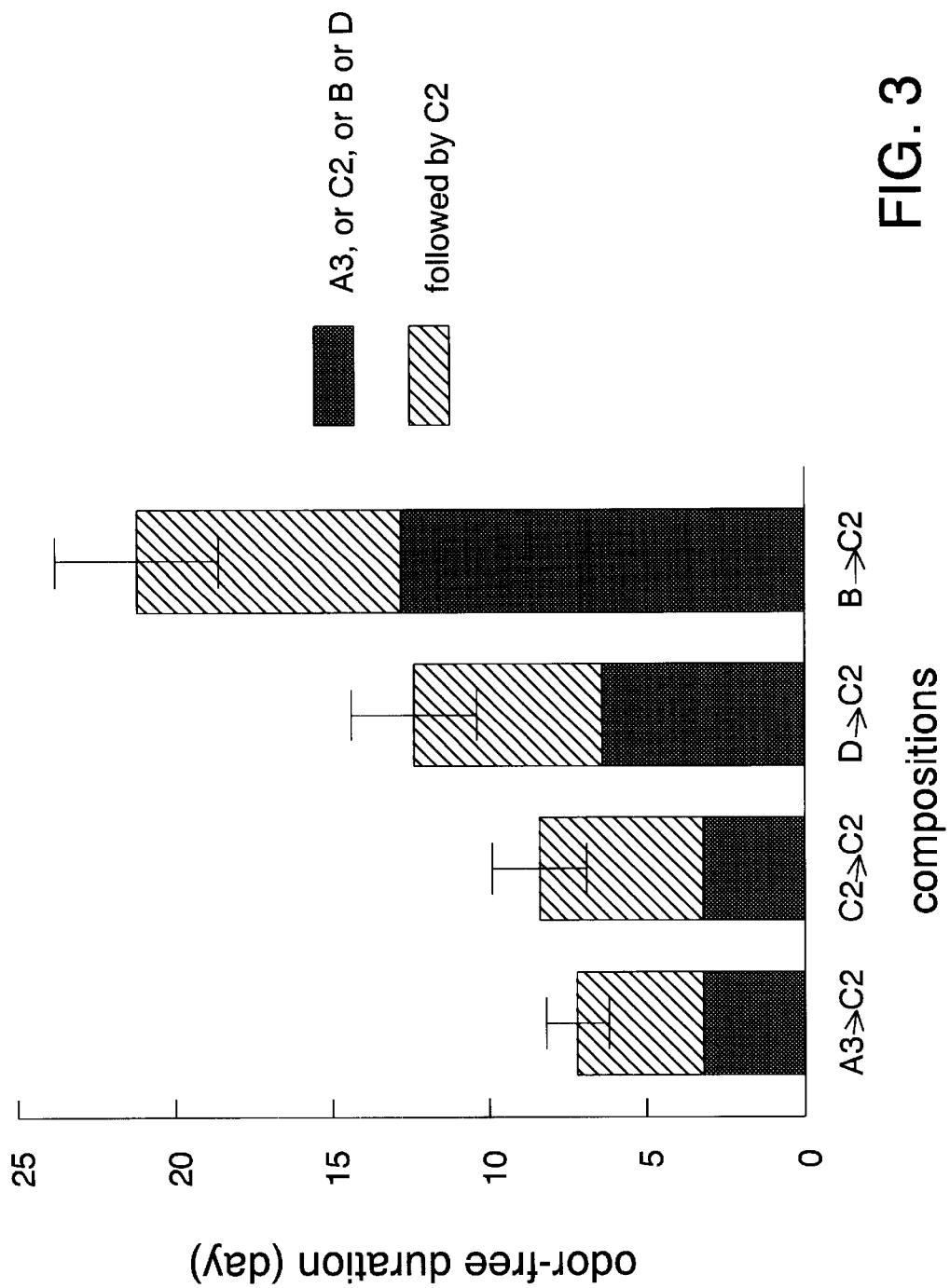
FIG. 3. is a graph of the deodorant effect of composition B (resveratrol, inonensin, aluminum chlorohydrate and zinc sulfate) followed by C2 (0.4% chlorhexidine diacetate), composition D followed by C2, composition A3 followed by C2, or C2 followed by C2. The test was carried out as described in Example 4.

Twenty subjects who have an average odor score of 3.5 (range from score 3–5) were randomly divided into 4 groups (five subjects/each group) to test different products followed by chlorhexidine digluconate. The subjects were instructed to take a shower in the evening using ordinary soap to clean the body surfaces before testing. After the skin was dried the different products and the positive control product A3 (8.2% aluminum chlorohydrate plus 0.5% zinc sulfate) were topically applied to one axilla, versus control vehicle in other. The subjects then go about their normal business. At 24 hour intervals, each subject was evaluated for underarm odor by averaging scores of three assessors until underarm odor was detectable (score 1 or up). 0.4% chlorhexidine diacetate was then applied to same axilla. Again, subjects were evaluated for underarm odor at each 24 hour period until odor was detectable (score 1 or up), It can be also seen from FIG. 3 that composition B followed by chlorhexidine diacetate was much more effective than the positive control followed by chlorhexidine diacetate and any one of the other tested products followed by chlorhexidine diacetate

What is claimed is:

1. A composition for preventing sweat-related odor by interfering with the odor-producing course for topical application to human skin, comprising;

a. an effective amount of an inhibitor of androgen receptor expression selected from group consisting of resveratrol, epigallocatechin-3-gallate, and flufenamic acid;

b. an effective amount of a substance of anti-DHT activity selected from group consisting of zinc gluconate, zinc glycerinate, zinc acetate, zinc sulfate, zinc oxide, zinc citrate, and zinc chloride;

c. an effective amount of a substance to inhibit odorant carrier proteins selected from a group consisting of monensin, tunicamycin, amphmycin, diumycin, showdomycin, tsushimycin, amphortericine, mycospocidin, streptovirudin, and D-glucosamine;

d. an effective amount of an antiperspirant selected from a group consisting of aluminum chlorohydrate, aluminum chloride, and aluminum zirconium;

e. an effective amount of the antimicrobial agent selected from a group consisting of chlorhexidine digluconate and chlorhexidine diacetate; and f. a cosmetically acceptable carrier.

2. A composition according to claim 1, wherein the inhibitor of androgen receptor expression is resveratrol in an amount of from 0.01% to 10% by weight of the composition.

3. A composition according to claim 1, wherein the substance of anti-DHT activity is zinc sulfate in an amount of from 0.01% to 5% by weight of the composition.

4. A composition according to claim 1, wherein the inhibitor of odorant carrier protein is monensin in an amount of from 0.01% to 5% by weight of the composition.

5. A composition according to claim 1, wherein the antiperspirant is an aluminum chlorohydrate in an amount of from 0.1% to 40% by weight of the composition.

6. A composition according to claim 1, wherein the antimicrobial agent is chlorhexidine digluconate in an amount of from 0.001% to 1% by weight of the composition.

* * * * *